United States Patent
Sumida et al.

(10) Patent No.: US 7,368,252 B2
(45) Date of Patent: May 6, 2008

(54) AGGLUTINATION ACCELERATOR FOR IMMUNOLOGICAL MEASUREMENT

(75) Inventors: Kyoichi Sumida, Amagasaki (JP); Koji Wada, Amagasaki (JP); Kazuhiko Ishihara, Bunkyo-ku (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 278 days.

(21) Appl. No.: 10/626,502

(22) Filed: Jul. 23, 2003

(65) Prior Publication Data

US 2004/0157276 A1  Aug. 12, 2004

(30) Foreign Application Priority Data

Jun. 5, 2001 (JP) ............... 2001-169051

(51) Int. Cl.
*G01N 33/567* (2006.01)
(52) U.S. Cl. .................. 435/7.21; 735/7.11; 735/7.2; 735/7.23
(58) Field of Classification Search ................. 435/7.1, 435/7.2, 7.23
See application file for complete search history.

(56) References Cited

U.S. PATENT DOCUMENTS

| 4,401,765 | A  | * | 8/1983 | Craig et al. ............ 436/533 |
| 6,248,597 | B1 | * | 6/2001 | Eda et al. ............. 436/518 |

FOREIGN PATENT DOCUMENTS

| EP | 1314982 A1 | * | 5/2003 |
| JP | 7-83923 | | 3/1995 |
| JP | 10-45794 | | 2/1998 |
| JP | 2000093169 A2 | * | 4/2000 |
| JP | 2000-239696 | | 9/2000 |
| JP | 2001-228149 | | 8/2001 |
| JP | 2002-22740 | | 1/2002 |
| JP | 2002-365296 | | 12/2002 |
| WO | WO 0218953 A1 | * | 3/2002 |

OTHER PUBLICATIONS

Sakaki et al. J. Biomedical Materials Research 1999; 47: 523-528.*

* cited by examiner

*Primary Examiner*—Brandon Fetterolf
(74) *Attorney, Agent, or Firm*—Hamre, Schumann, Mueller & Larson, P.C.

(57) ABSTRACT

An object of the present invention is to provide an immunoassay of PSA using an agglutination accelerator, which has an agglutination accelerating effect equal to or stronger than the known agglutination accelerator; hardly generates non-specific turbidity; and hardly generates salting out even in a solution with a high salt concentration. The present invention relates to an immunoassay of a prostate-specific antigen comprising performing an antigen-antibody reaction in the presence of a polymer having a monomer unit derived from a monomer represented by the following general formula [2]:

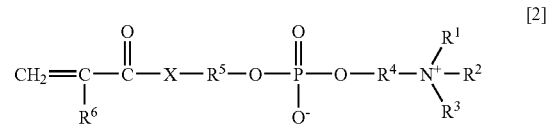

(wherein $R^1$-$R^3$ are each independently a hydrogen atom or an alkyl group optionally having a hydroxyl group; $R^4$ is an alkylene group; $R^5$ is an alkylene group optionally having a substituent and optionally having an oxygen atom in a chain; $R^6$ is a hydrogen atom or a methyl group, and X is an oxygen atom or a —NH— group), and a kit of reagent for an immunoassay comprising a reagent containing an agglutination accelerator for the immunoassay.

8 Claims, 1 Drawing Sheet

AGGLUTINATION ACCELERATOR FOR IMMUNOLOGICAL MEASUREMENT

DETAILED DESCRIPTION OF THE INVENTION

Prior Art

A method for confirming presence of a target substance in a sample or measuring a concentration of a target substance in a sample by observing formation of agglutination after mixing immobilized antigen or antibody on a proper carrier and a biological origin sample such as serum, plasma, urine, and the like, or a method for confirming presence of a target substance in a sample or measuring a concentration of a target substance in a sample on the basis of turbidity generated by an antigen-antibody reaction, is an assay method known as so-called immunoassay.

In a case of measuring agglutination or turbidity caused by the antigen-antibody reaction, various compounds so-called agglutination accelerator are generally used. The agglutination accelerator has an action to generate more easily an agglutination based on the antigen-antibody reaction. Examples of such agglutination accelerators are, for example, polyethylene glycol, dextran, carboxymethyl cellulose, hydroxyethyl cellulose, and the like, and among them polyethylene glycol is commonly used.

Since polyethylene glycol is salted out in a solution of high salt concentration, one of major problems is to worsen the accuracy of measurement caused by hightning blank value of the reagent when such solution is used as reagent for immunoassay.

On the other hand, there is recently a trend that a high sensitive assay method is performed by utilizing agglutination or turbidity generated by the antigen-antibody reaction. As a result, there is a demand for development of the agglutination accelerator, which has an agglutination accelerating effect equal to or stronger than the conventionally used polyethylene glycol; hardly generates non-specific turbidity; and hardly generates salting out even in a solution with a high salt concentration.

Means for Solving the Problem

The present invention has been completed considering these situations. An object of the present invention is to provide an immunoassay of prostate-specific antigen (PSA) using an agglutination accelerator, which has an agglutination accelerating effect equal to or stronger than the conventionally known agglutination accelerator; hardly generates non-specific turbidity; and hardly generates salting out even in a solution with a high salt concentration, and a kit of reagent for the immunoassay comprising the reagent containing said agglutination accelerator. Another object of the present invention is to provide the following as the means thereof.

That is, the present invention relates to: (1) An immunoassay of a prostate-specific antigen comprising performing an antigen-antibody reaction in the presence of a polymer having a monomer unit derived from a monomer represented by the following general formula [2]:

(wherein, $R^1$ to $R^3$ are each independently a hydrogen atom

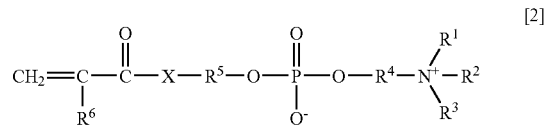

or an alkyl group optionally having a hydroxyl group; $R^4$ is an alkylene group; $R^5$ is an alkylene group optionally having a substituent and optionally having an oxygen atom in the chain; $R^6$ is a hydrogen atom or a methyl group; and X is an oxygen atom or a —NH— group).

(2) A kit of reagent for immunoassay of a prostate-specific antigen comprising combining a reagent containing:

a copolymer obtained by polymerizing a monomer represented by the following general formula [2]:

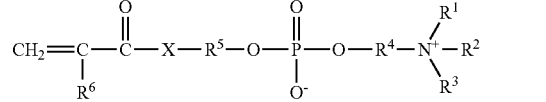

(wherein, $R^1$ to $R^3$ are each independently a hydrogen atom or an alkyl group optionally having a hydroxyl group; $R^4$ is an alkylene group; $R^5$ is an alkylene group optionally having a substituent and optionally having an oxygen atom in the chain; $R^6$ is a hydrogen atom or a methyl group; and X is an oxygen atom or a —NH— group), and a monomer selected from a group consisting of acrylic acid or acrylate ester, methacrylic acid or methacrylate ester, acrylamide or N-substituted deriveatives thereof, methacrylamide or N-substituted deriveatives thereof, and styrene or derivatives thereof; and a reagent containing an antibody to the prostate-specific antigen or a prostate-specific antigen.

Namely, the present inventors extensively studied to find out an immunoassay of PSA using an agglutination accelerator, which has an agglutination accelerating effect equal to or stronger than that of the known agglutination accelerator; hardly generates non-specific turbidity; and hardly generates salting out even in a solution with a high salt concentration, and a kit of reagent for the immunoassay comprising a reagent containing the agglutination accelerator for the immunoassay, and finally found out that the polymer represented by the general formula [2] (hereinafter sometimes abbreviated as the polymer of the present invention) had the intended properties, and thus the present invention was completed.

BEST MODE FOR CARRYING OUT THE INVENTION

Figure 1:
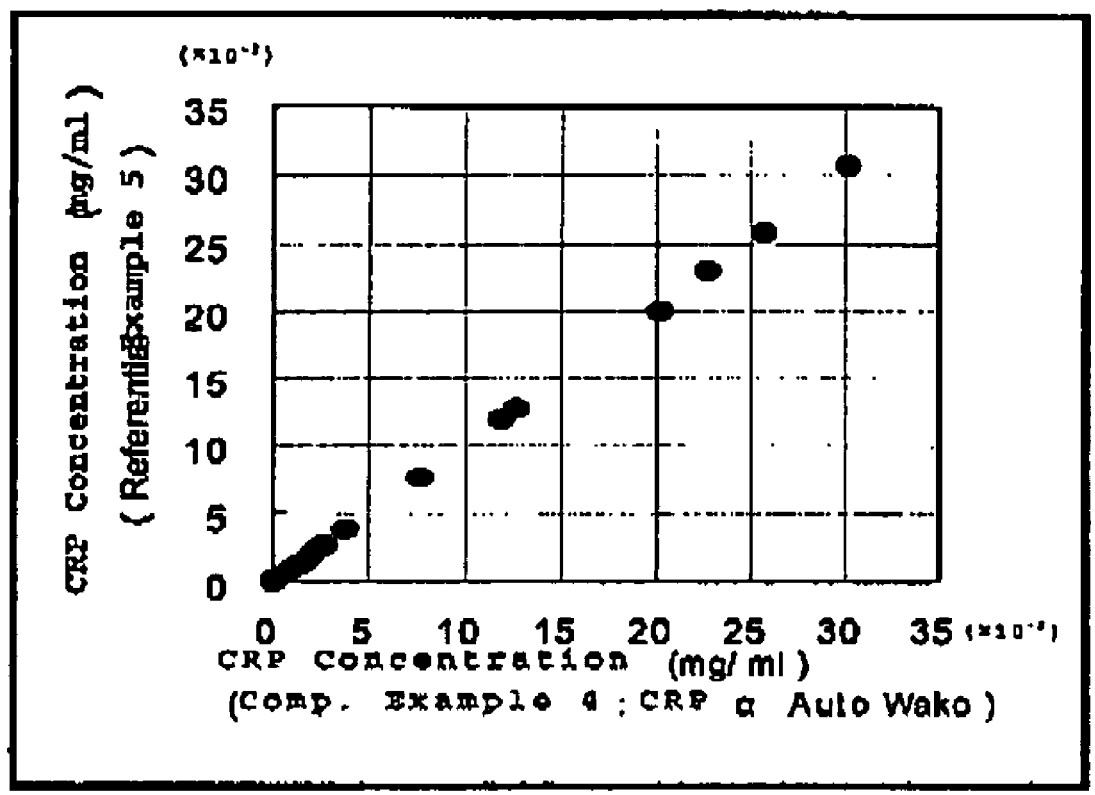
FIG. 1 is a drawing which shows a correlation between CRP concentration (mg/mL) obtained in Referential Example 5 and CRP concentration (mg/mL) obtained in Comparative Example 4.

The polymer used as an agglutination accelerator in the present invention is not particularly limited and may be a homopolymer or a copolymer, usually having a molecular weight of 10,000 to 1,000,000, preferably 10,000 to 500,000, and more preferably 50,000 to 500,000.

More specifically, the polymerpreferably includes a polymer having a monomer unit derived from a monomer represented by the following general formula [2]:

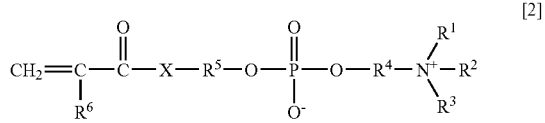

wherein, $R^1$ to $R^3$ are each independently a hydrogen atom or an alkyl group optionally having a hydroxyl group; $R^4$ is an alkylene group; $R^5$ is an alkylene group optionally having a substituent and optionally having an oxygen atom in the chain; $R^6$ is a hydrogen atom or a methyl group; and X is an oxygen atom or a —NH— group.

In the above-describedgeneral formula [2], analkyl group optionally having a hydroxyl group represented by $R^1$ to $R^3$ may be linear, branched or cyclic, and usually includes a group having 1-22 carbon atoms, preferably 1 to 20 carbon atoms, more preferably 1 to 2 carbon atoms, and further more preferably 1, and specifically includes sucha group as methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, tert-hexyl, cyclopropyl, cyclohexyl, cyclopentyl, lauryl, myristyl, palmityl and stearyl group, and methyl group, ethyl group and the like are preferable, and methyl group and the like is more preferable.

The alkyl group having a hydroxyl group includes a group in which 1 to 2 hydrogen atoms, preferably one hydrogen atom in the above-described alkyl group are substituted with a hydroxyl group, and specifically includes a group such as hydroxymethyl, hydroxyethyl, hydroxy-n-propyl, hydroxy-isopropyl, hydroxy-n-butyl, hydroxyisobutyl, hydroxy-sec-butyl, hydroxy-tert-butyl, hydroxy-n-pentyl, hydroxyiso-pentyl, hydroxy-sec-pentyl, hydroxy-tert-pentyl, hydroxy-n-hexyl, hydroxyisohexyl, hydroxy-sec-hexyl, hydroxy-tert-hexyl, hydroxycyclopropyl, hydroxycyclohexyl and hydroxycyclopentyl group, and hydroxymethyl group and hydroxyethyl group are preferable.

The alkylene group represented by $R^4$ includes, for example, an alkylene group having 1 to 6 carbon atoms, preferably 2 to 3 carbon atoms, and may be linear, branched orcyclic, and specifically includes a group such as methylene, ethylene, propylene, trimethylene, butylene, 1-ethylethylene, 2-methyltrimethylene, 2-ethyltrimethylene, hexylene, cyclopropylene, cyclobutylene, cyclopentylene and cyclohexylene group, and ethylene group, propylene group and trimethylene group are preferable.

In the alkylene group represented by $R^5$ in the above-described general formula [2], an alkylene group, optionally having a substituent and optionally having an oxygen atom in the chain, which does not have an oxygen atom includes, for example, the group having 1 to 10 carbon atoms, preferably 1 to 6 carbon atoms and more preferably 2 to 6 carbon atoms, which may be linear, branched or cyclic. The alkylene group specifically includes, for example, a group such as methylene, ethylene, propylene, trimethylene, butylene, 1-ethylethylene, 2-methyltrimethylene, 2-ethyltrimethylene, hexylene, cyclopropylene, cyclobutylene, cyclopentylene and cyclohexylene group. The above substituent includes, for example, an alkoxy group having 1 to 6 carbon atoms, preferably 1 to 3 carbon atoms, and may be linear, branched or cyclic, and specifically includes, for example, a group such as methoxy, ethoxy, n-propoxy, isopropoxy, n-butoxy, isobutoxy, sec-butoxy, tert-butoxy, n-pentyloxy, isopentyloxy, sec-pentyloxy, tert-pentyloxy, n-hexyloxy, isohexyloxy, sec-hexyloxy, tert-hexyloxy, cyclopropoxy, cyclohexyloxy and cyclopentyloxy group; and a halogen atom, more specifically fluorine, chlorine, bromine and iodine atom. A group such as ethylene, propylene, trimethylene and butylene group is preferable. When the group has an oxygen atom in the chain, number of said oxygen atom is 1 to 5, preferably 1 to 3, and the group specifically includes, for example, a group represented by —$(C_2H_4O)_n$—$C_2H_4$— (wherein, n is an integer of 1 to 5).

When the polymer, having a monomer unit derived from a monomer represented by the above-described general formula [2], is a copolymer, a monomer unit other than the monomer unit derived from a monomer represented by the above-described general formula [2] includes an unit derived from a monomer selected from, for example, acrylic acid or acrylate ester, methacrylic acid or methacrylate ester, acrylamide or N-substituted derivatives thereof, methacrylamide or N-substituted derivatives thereof, and styrene or derivatives thereof. Besides, two or more kinds of these monomer units may be contained in a copolymer.

Said acrylate ester includes alkyl acrylate, aralkyl acrylate and the like, the methacrylate ester include alkyl methacrylate ester, aralkyl methacrylate ester and the like; the N-substituted acrylamides include N-alkyl acrylamide and N-aralkyl acrylamide; the N-substituted methacrylamides include N-alkyl methacrylamide and N-aralkyl methacrylamide; and the styrene derivatives include α-methylstyrene, substituted styrene, substituted α-methylstyrene and the like.

The alkyl group in the above-described alkyl acrylate ester, alkyl methacrylate ester, N-alkyl acrylamides and N-alkyl methacrylamides may be linear, branched or cyclic, and usually has 1-6 carbon atoms, more preferably 1-4 carbon atoms, and specifically includes, for example, a group suchasmethyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, tert-hexyl, cyclopropyl, cyclohexyl and cyclopentyl group. Said alkyl group may have a substituent, which includes, for example, trialkylammonio group (wherein, an alkyl group includes, for example, methyl group, ethyl group, n-propyl group and isopropyl group having 1-3 carbon atoms. When an alkyl group has a trialkylammonio substituent, said substituent is positively charged and thus usually bound with a counter ion. Such a counter ion includes a halogen ion such as fluorine, chlorine, bromine and iodine ion).

The aralkyl group in aralkyl acrylate ester, aralkyl methacrylate ester, N-aralkyl acrylamides and N-aralkyl methacrylamides includes an aralkyl group having 7 to 10 carbon atoms, and specifically includes, for example, a group such as benzyl, phenylethyl, phenylpropyl and phenylbutyl groups.

The substituent which may be possessed by styrene or α-methylstyrene includes, for example, alinear, branched or cyclic alkyl group usually having 1 to 6 carbon atoms, more preferably 1 to 4 carbon atoms (specifically including, for example, a group such as methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, tert-hexyl, cyclopropyl, cyclohexyl and cyclopentyl group); a linear, branched or cyclic alkoxy group usually having 1 to 6 carbon atoms, more preferably 1 to 4 carbon atoms (specifically including, for example, a group such as methoxy, ethoxy, n-propoxy, isopropoxy, n-butoxy, isobutoxy, sec-butoxy, tert-butoxy, n-pentyloxy, isopentyloxy, sec-pentyloxy, tert-pentyloxy, n-hexyloxy, isohexyloxy, sec-hexyloxy, tert-hexyloxy, cyclopropoxy, cyclohexyloxy and cyclopentyloxy group); a halogen atom such as fluorine, chlorine, bromine and iodine atom; a carboxyl group; a hydroxyl group and an amino group.

Specific examples of these monomers include, for example, methacrylic acid, methyl methacrylate, ethyl methacrylate, propyl methacrylate, butyl methacrylate, 2-ethylhexyl methacrylate, lauryl methacrylate, stearyl methacrylate, 2-trimethylammonioethyl methacrylate, benzyl methacrylate, phenylethyl methacrylate; acrylic acid, methyl acrylate, ethyl acrylate, butyl acrylate, 2-ethylhexyl acrylate, lauryl acrylate, stearyl acrylate, 2-trimethylammonioethyl acrylate, benzyl acrylate, phenylethyl acrylate; acrylamide, N-methylacrylamide, N-ethylacrylamide, N-butylacrylamide, N-2-ethylhexylacrylamide, N-laurylacrylamide, N-stearylacrylamide, N-2-trimethylammonioethylacrylamide, N-benzylacrylamide, N-phenylethylacrylamide; methacrylamide, N-methylmethacrylamide, N-ethylmethacrylamide, N-butylmethacrylamide, N-2-ethylhexylmethacrylamide, N-laurylmethacrylamide, N-stearylmethacrylamide, N2-trimethylammonioethylmethacrylamide, N-benzylmethacrylamide, N-phenylethylmethacrylamide; styrene, caroboxystyrene, hydroxystyrene, aminostyrene, methylstyrene, ethylstyrene, methoxystyrene, ethoxystyrene, chlorostyrene, bromostyrene, α-methylstyrene, α-methyl-carboxystyrene, α-methyl-hydroxystyrene, α-methyl-aminostyrene, α-methyl-methylstyrene, α-methyl-ethylstyrene, α-methyl-methoxystyrene, α-methyl-ethoxystyrene, α-methyl-chlorostyrene, α-methyl-bromostyrene; polyoxyethylene methacrylate, N,N,N-triethyl[2-(methacryloyloxy)ethyl]ammoniumbromide, N,N,N-trimethyl[2-(methacryloyloxy)ethyl]ammoniun chloride, N,N-diethyl-N-propyl[2-(methacryloyloxy)ethyl] ammonium bromide, N,N,N-trimethyl[3-(methacryloyloxy)-2-hydroxypropyl]ammonium chloride (QM) and N,N,N-trimethylammonium-methylstyrenebromide. Among them, methacrylic acid, stearyl methacrylate, benzyl methacrylate, buthyl methacrylate, polyoxyethylene methacrylate and N,N,N-trimethyl[3-(methacryloyloxy)-2-hydroxypropyl]ammonium chloride (QM) are preferable, and benzyl methacrylate is more preferable.

In the copolymer, a ratio of the monomer unit derived from a monomer represented by the general formula [2], is usually not less than 20% and less than 100%, preferably 30 to 95%, more preferably 30-90% and furthermore preferably 60 to 90%.

As the polymer having a monomer unit derived from a monomer represented by the general formula [2] in accordance with the present invention, either a commercially available polymer or a polymer synthesized according to the method described in JP-A-10-45794 and JP-A-2000-239696 maybe used. The agglutination accelerator of the present invention comprises a polymer having a monomer unit derived from the monomer represented by the general formula [2], as described hereinabove. The agglutination accelerator is used, for example, by properly dissolving in various reagents (usually in a form of solution) used in the known immunoassay, in which a target substance is measured based on agglutination and the like derived from an antigen-antibody reaction such as immunoturbidimetry, immunonephelometry, latex agglutination, preferably by dissolving in reagents used in the immunoturbidimetry or the latex agglutination, and more preferably by dissolving in reagents used in the latex agglutination. Concentration of the agglutination accelerator used in the various reagents is generally 0.1 to 20% by W/V, preferably 0.1 to 10% by W/V, more preferably 0.1 to 5% by W/V and further more preferably 0.1 to 2.0% by W/V, as a concentration in the reaction solution of the antigen-antibody reaction. The reaction under such concentration results in suppressing the increase of the blank value within a range not affecting the assay, and as a result, the agglutination accelerating effect of the present invention can be exhibited sufficiently.

In addition, the assay of the present invention may be performed by using various reagents used in the known immunoassay, in which a target substance is measured based on agglutination and the like derived from the antigen-antibody reaction such as immunoturbidimetry, immunonephelometry, latex agglutination, according to the known operation method, except that the assay is performed under the coexistence of the polymer of the present invention or the reagent kit of the present invention admixed at the above concentration on the antigen-antibody reaction.

Examples of buffers used in the assay of the present invention include every buffer generally used in the immunoturbidimetry and immunonephelometry such as Tris buffer, phosphate buffer, veronal buffer, borate buffer and Good's buffer. A pH in the assay is not particularly limited so long as it is within a range not suppressing the antigen-antibody reaction, and generally is suitably selected from a range of 6 to 10. A method measuring scattered light (nephelometry) can be performed, for example, according to the description in "Principles of Clinical Laboratory Tests" 30th Ed., 2nd copy, p. 051-853 (1993), Kanehara Publ Co. Ltd. A method measuring transmitted light (immunoturbidimetry) can be performed, for example, according to the description in "Principles of Clinical Laboratory Tests" 30th Ed., 2nd Copy, p. 853-854 (1993), Kanehara Publ. Co. Ltd. The latex agglutination test, in which a target substance is assayed based on the result obtained by measuring an extent of agglutination of latex sensitized(immobilized) with an antibody or an antigen to the target substance based on a change of scattered light or transmitted light, can be performed, for example, according to the description in "New Actual Cases of Immunoassay, and Applications to Developments of Diagnostic Reagents and Drugs", p. 103-187, Keiei KyoikuPubl. Co. Ltd. The measurement of scattered light or transmitted light in the nephelometry, immunoturbidimetry and latex agglutination can be performed by using a multipurpose biochemical analyzer such as automatic analyzer and spectrophotometer and a special-purpose apparatus for nephelometry such as laser nephelometry. Details can be provided by a manual of each apparatus.

The reagent kit of the present invention comprises a combination of the reagent containing a copolymer obtained by polymerizing the monomer represented by the general formula [2] and a monomer selected from a group consisting of acrylic acid or acrylate ester, methacrylic acid or methacrylate ester, acrylamide or N-substituted deriveatives thereof, methacrylamide or N-substituted deriveatives thereof, and styrene or derivatives thereof, and the reagent containing an antibody to a prostate-specific antigen or a prostate-specific antigen. Specific examples of the monomer represented by the general formula [2] and a monomer selected from a group consisting of acrylic acid or acrylate ester, methacrylic acid or methacrylate ester, acrylamide or N-substituted deriveatives thereof, methacrylamide or N-substituted deriveatives thereof, and styrene or derivatives thereof are described as above. Further, guanidine or arginine, which has an action to suppress non-specific reaction of the antigen-antibody reaction, maybe added to the reagent containing the copolymer obtained by polymerizing the monomer represented by the general formula [2] and a monomer selected from a group consisting of acrylic acid or acrylate ester, methacrylic acid or methacrylate ester, acrylamide or N-substituted derivatives thereof, methacrylamide or N-substituted derivatives thereof, and styrene or derivatives thereof. Amount thereof to be added is not particularly limited so long as the intended effect can be obtained, and is preferably 100 to 700 mM for guanidine and 100 to 400 mM for arginine.

The antibody to prostate-specific antigen or the prostate-specific antigen in the reagent containing the antibody to prostate-specific antigen or the prostate-specific antigen may be fixed on a carrier or the like, and a preferable carrier is, for example, latex and the like.

Further, the above reagent kit may optionally containa buffer (for example, Tris buffer, phosphate buffer, veronal buffer, borate buffer and Good's buffer), a stabilizier agent (for example, albumin, globulin, water-soluble gelatin, surface active agent, sugars), an antiseptic (for example, salicylic acid, benzoic acid, sodium azide), and a reagent which are used in this field and do not inhibit stability of coexisting reagent or not inhibit the antigen-antibody reaction. Concentration thereof in use may be within a range of the concentration generally used in this field.

As obvious from the above, the present invention provides an immunoassay of PSA using an agglutination accelerator, which has an agglutination accelerating effect equal to or stronger than that of the conventionally known agglutination accelerator; hardly generates non-specific turbidity; and hardly generates salting out even in a solution with a high salt concentration, and a reagent kit comprising combining a reagent containing said agglutination accelerator and the reagent containing an antibody to PSA or the PSA. Since the agglutination accelerator can exhibit an agglutination accelerating effect equal to or stronger than the action of the conventional means even in a high salt concentration, and makes the non-specific turbidity difficult to occur, a PSA assay with high precision can be achieved.

The present invention will be explained by the following Examples, but the present invention is not limited by these Examples.

EXAMPLES

Synthesis Example 1

Synthesis of a Copolymer of 2-methacryloyloxyethylphosphorylcholine (MPC) and n-butyl methacrylate (BMA)

8:2

A glass reaction tube for polymerization was charged with 4.7 g (16 mM) of MPC and 0.57 g (4 mM) of BMA, then further added with 0.03 g of 2,2'-azobisisobutylonitrile (AIBN) as a polymerization initiator and 20 ml of methanol as a polymerization solvent. The air in the reaction tube was sufficiently exchanged with argon, and the reaction tube was sealed. Then polymerization reaction was conducted at 60° C. for 24 hours. The obtained reaction mixture was ice-cooled, then added with 400 ml of diethyl ether drop-wisely to precipitate the polymer. Said precipitate was filtered, washed sufficiently with diethyl ether and dried under reduced pressure to obtain a polymer as a white powder. The polymer thus obtained was named polymer 1. A molecular weight of polymer 1 was 600,000.

Synthesis Example 2

Synthesis of a copolymer of MPC/BMA

5:5

A similar synthesis as in the above-described Synthesis Example 1 was repeated except that 20 mM in total of MPC and BMA were used in a molar ratio of 5:5, to obtain polymer 2. A molecular weight of polymer 2 was 338,000.

Synthesis Example 3

Synthesis of a Copolymer of MPC/BMA 3.7

A similar synthesis as in the above-described Synthesis Example 1 was repeated except that 20 mM in total of MPC and BMA were used in a molar ratio of 3:7, to obtain polymer 3. A molecular weight of polymer 3 was 92,000.

Synthesis Example 4

Synthesis of a copolymer of MPC/stearyl methacrylate

9:1

A similar synthesis as in the above-described Synthesis Example 1 was repeated except that stearyl methacrylate was used instead of BMA and 20 mM in total of MPC and stearyl methacrylate were used in a molar ratio of 9:1, to obtain polymer 4. A molecular weight of polymer 4 was 130,000.

Synthesis Example 5

Synthesis of a Copolymer of MPC/benzyl methacrylate

8:2

A similar synthesis as in the above-described Synthesis Example 1 was repeated except that benzyl methacrylate was used instead of BMA and 20 mM in total of MPC and benzyl methacrylate were used in a molar ratio of 8:2, to obtain polymer 5. A molecular weight of polymer 5 was 240,000.

Synthesis Example 6

Synthesis of a Homopolymer of MPC

A glass reaction tube for polymerization was charged with 5.9 g (20 mM) of MPC, then further added with 0.03 g of 2,2'-azobisisobutylonitrile (AIBN) as a polymerization initiator and 20 ml of methanol as a polymerization solvent. The air in said reaction tube was sufficiently exchanged with argon, and the reaction tube was sealed. Then polymerization reaction was conducted at 50° C. for 24 hours. The reaction mixture was ice-cooled, then added with 400 ml of diethyl ether drop-wisely to precipitate the polymer. The precipitate obtained was filtered, washed sufficiently with diethyl ether and dried under a reduced pressure to obtain a polymer as a white powder. The polymer thus obtained was named polymer 6. A molecular weight of polymer 6 was 110,000.

Synthesis Example 7

Synthesis of a Copolymer of MPC/Qm

9:1

A similar synthesis as in the above-described Synthesis Example 1 was repeated except that QM was used instead of BMA and 20 mM in total of MPC and QM were used in a molar ratio of 9:1, to obtain polymer 7. A molecular weight of polymer 7 was 33,000.

Synthesis Example 8

Synthesis of a Copolymer of MPC/Methacrylic Acid

3:7

A similar synthesis as in the above-described Synthesis Example 1 was repeated except that methacrylic acid was used instead of BMA and 20 mM in total of MPC and methacrylic acid were used in a molar ratio of 3:7, to obtain polymer 8. A molecular weight of polymer 8 was 288,000.

Example 1

Assay of Prostate-Specific Antigen (PSA) by LIA (Effect of Polymer Type on the Agglutination Accelerating Action)

(1) Preparation of an Anti-Human PSA antibody Sensitized Latex Test Solution

A mixture of 0.5 ml of 50 mM borate buffer (pH 7.1) containing 0.6 mg of anti-human PSA mouse monoclonal antibody (made by Wako Pure chemical Industries, Ltd.) and 0.5 ml of 50 mm borate buffer (pH 7.1) containing a polystyrene latex (particle size 0.22 μm, made by Sekisui Chem. Co. Ltd.) suspended in 2% by W/V, was reacted at 25° C. for 2 hours. Subsequently, the latex separated by centrifugation was washed with 50 mM borate buffer (pH 7.1), and said latex was suspended in 50 mM borate buffer (pH 7.3) containing 0.5% by W/V of BSA so that the concentration of the latex became 0.1 k by W/v, and the thus obtained mixture was used as an anti-human PSA antibody sensitized(immobilized) latex test solution.

(2) Sample

A PSA derived from human seminal fluid (made by Wako Pure Chemical Industries, Ltd.) was dissolved in 10 mM phosphate buffer (0.85% NaCl) containing 1.0% by W/V of BSA, and the PSA solution of a predetermined concentration was used as a sample.

(3) Reagents i) Test solution No. 1

A solution of 100 mM REPES-NaOH buffer (pH 7.0) containing 1.5% of a polymer as an agglutination accelerator, 0.1% of BSA and 2% of NaCl, or a solution of 100 mM HEPES-NaOH buffer (pH 7.0) containing 0.1% of BSA and 2% of NaCl as a reagent without agglutination accelerator was designated as test solution No. 1.

ii) Test solution No. 2

The anti-human PSA antibody sensitized (immobilized) latex test solution prepared in (1) was used as a test solution NO. 2.

(4) Assay method

Assay was performed under the following measuring conditions by using a BM-8 automatic analyzer made by JEOL Ltd.

| | |
|---|---|
| Sample: | 5 μl |
| Test solution No. 1: | 90 μl |
| Test solution No. 2: | 30 μl |
| Assay method: | 2 point end method (34-65) |
| Main wavelength: | 571 nm |

(5) Results

The values of absorbance (turbidity) obtained are shown in Table 1. The value in the Table was calculated by subtracting the absorbance value for the reagent blank from the value obtained for the test solution, and then multiplying by 10,000.

Comparative Example 1

The reagent as same as in Example 1 was used and the measurement as same as in Example 1 was repeated, except that the polymers of the present invention were replaced by PEG 6000 with a concentration of 1.5%.

The results obtained are shown in Table 1 together with the results obtained in Example 1.

TABLE 1

| PSA (ng/mL) | Without Agglutination accelerator | Example 1 | | | Comp. Example 1 |
|---|---|---|---|---|---|
| | | Polymer 1 | Polymer 5 | Polymer 6 | PEG 6000 |
| 2 | 37 | 71 | 90 | 60 | 75 |
| 10 | 160 | 512 | 605 | 296 | 292 |
| 50 | 817 | 5483 | 5824 | 2440 | 1914 |

As obvious from the results in Table 1, the agglutination accelerating action was observed in the assay of PSA, by using any polymer of the present invention. In addition, as compared with the results of PEG 6000, it can be understood that every polymer of the present invention could exhibit a higher agglutination accelerating action than that of PEG 6000, and among them the polymer 5 exhibited the highest effect in these 3 polymers.

Example 2

Assay of PSA by LIA

Effect of Polymer Concentration on Agglutination Accelerating Action (1) Sample

A PSA derived from human seminal fluid (made by Wako Pure Chemical Industries, Ltd.) was dissolved in 10 mM phosphate buffer (0.85% NaCl) containing 1.0% by W/V of BSA, and the PSA solution with a predetermined concentration was used as a sample.

(2) Reagents i) Test Solution No. 1

A solution of 100 mM HEPES-NaOH buffer (pH 7.0) containing a predetermined concentration of the polymer S as an agglutination accelerator, 0.1% of BSA and 2% of Nacl, or a solution of 100 mM HEPES-NaOH buffer (pH 7.0) containing 0.1% of BSA and 2% of Nacl as a reagent without agglutination accelerator was designated as test solution No. 1.

ii) Test Solution No. 2

The anti-human PSA antibody sensitized (immobilized) latex test solution obtained and prepared in Example 1 was used as test solution No. 2.

(3) Assay Method

Assay was performed under the following measuring conditions by using a BM-8 automatic analyzer made by JEOL Ltd.

| | |
|---|---|
| Sample: | 5 μl |
| Test solution No. 1: | 90 μl |
| Test solution No. 2: | 30 μl |
| Assay method: | 2 point end method (34-65) |
| Main wavelength: | 571 nm |

(4) Results

The values of absorbance (turbidity) obtained are shown in Table 2. The value in the Table was calculated by subtracting the absorbance value for the reagent blank from the value obtained for the test solution, then multiplying by 10,000.

TABLE 2

| PSA (ng/mL) | Without Agglutination Accelerator | Example 2 | | |
|---|---|---|---|---|
| | | 1.0% Addition | 1.5% Addition | 2.0% Addition |
| 2 | 37 | 58 | 90 | 833 |
| 10 | 160 | 318 | 605 | 3869 |
| 50 | 817 | 3096 | 5824 | 7454 |

As obvious from the results in Table 2, it can be understood that the agglutination accelerator action of the polymer 5 in the assay by LIA is increased depending on the increase in the concentration of polymer 5.

Referential Example 1

Assay of CRP by Latex Immunoturbidimetric Assay

LIA (1) Preparation of an Anti-Human CRP Antibody Sensitized Latex Test Solution A mixture of 2 ml of 50 mM borate buffer (pH 7.1) containing 1.1 mg of anti-human CRP goat polyclonal antibody (made by International Immunology Corp.) and 1 ml of 50 mM borate buffer (pH 7.1) containing a polystyrene latex (particle size 0.12 μm. made by Sekisui Chem. Co. Ltd.) suspended in 1% by W/V, was reacted at 30° C. for 2 hours. Subsequently, the latex separated by centrifugation was washed with 50 mM borate buffer (pH 7.1), and said latex was suspended in 50 mM borate buffer (pH 7,3) containing 0.5% by W/V of bovine serum albumin (BSA) so that the concentration of the latex became 0.2% by W/V. The thus obtained suspension was used as an anti-human CRP antibody sensitized(immobilized) latex test solution.

(2) Sample

Physiological saline solution (0.85% NaCl, CRP concentration: 0 mg/mL) was used as a sample for reagent blank assay, and solutions of CRP calibrator set (CRP concentration: 0.03 mg/mL, made by Wako Pure Chemical Industries, Ltd.) diluted into 10 steps of concentrations with physiological saline solution (0.85% NaCl) were used as samples for CRP-specific absorbance measurement.

(3) Reagents i) Test Solution No. 1

Previously synthesized polymer 1, polymer 5 and polymer 6 were used as the agglutination accelerator and a solution of 100 mM HEPES-NaOH buffer (pH 7.0) containing the predetermined concentration of the predetermined polymer, 0.1% of BSA and 1% of NaCl, or a solution of 100 mM HEPES-NaOH buffer (pH 7.0) containing 0.1% of BEA and 1; of NaCl as a reagent without agglutination accelerator, was designated as test solution No. 1.

ii) Test Solution No. 2

The anti-human CRP antibody sensitized (immobilized) latex test solution prepared in the above (1) was used as test solution No. 2.

(4) Assay Method

Assay was performed under the following measuring conditions by using a EM-8 automatic analyzer made by JEOL Ltd.

| | |
|---|---|
| Sample: | 1.25 μl |
| Test solution No. 1: | 75 μl |
| Test solution No. 2: | 25 μl |
| Assay method: | 2 point end method (34-65) |
| Main wavelength: | 571 nm |

(5) Results

The values of absorbance (turbidity) obtained are shown in Table 3. The value in the Table was calculated by subtracting the absorbance value of the reagent blank from the value obtained for the test solution, then multiplying by 10,000.

Comparative Example 2

The reagent as same as in Example 1 was used and the measurement as same as in Example 1 was repeated, except that the polymers of the present invention were replaced by PEG 6000 with the predetermined concentration, which was generally used as an agglutination accelerator.

The results obtained are shown in Table 3 together with the results in Referential Example 1.

TABLE 3

| CRP (mg/mL) | No Addition | Referential Example 1 | | | | | | Comparative Example 2 | |
|---|---|---|---|---|---|---|---|---|---|
| | | Polymer 1 | | Polymer 5 | | Polymer 6 | | PEG 6000 | |
| Addition Conc'n | 0 | 0.5% | 1.0% | 0.5% | 1.0% | 0.5% | 1.0% | 0.5% | 1.0% |
| 0.003 | 302 | 436 | 626 | 427 | 566 | 381 | 487 | 371 | 468 |
| 0.006 | 750 | 1143 | 1815 | 1067 | 1544 | 941 | 1220 | 922 | 1163 |
| 0.009 | 1310 | 2075 | 3600 | 1950 | 3024 | 1720 | 2266 | 1598 | 2056 |
| 0.012 | 1961 | 3221 | 5595 | 2965 | 4662 | 2566 | 3447 | 2405 | 3029 |
| 0.015 | 2723 | 4577 | 7367 | 4152 | 6230 | 3564 | 4673 | 3333 | 4096 |
| 0.018 | 3527 | 5906 | 8656 | 5367 | 7725 | 4657 | 6012 | 4254 | 5194 |
| 0.021 | 4346 | 7022 | 9242 | 6512 | 8672 | 5685 | 7042 | 5154 | 6100 |
| 0.024 | 5212 | 8017 | 9464 | 7506 | 9104 | 6511 | 7754 | 6066 | 6974 |
| 0.027 | 5991 | 8630 | 9512 | 8225 | 9421 | 7387 | 8424 | 6827 | 7612 |
| 0.030 | 6533 | 9011 | 9458 | 8690 | 9480 | 7919 | 8752 | 7356 | 7996 |

As obvious from the results in Table 3, the agglutination accelerating action was observed with any polymer of the present invention, In addition, as compared with the results of PEG 6000 in Comparative Example 2, it can be understood that every polymer of the present invention could exhibit a higher agglutination accelerating action than that of PEG 6000, in particular, polymer 1 and polymer 5 exhibit higher effects.

Referential Example 2

Assay of CRP in Human Serum by LIA (1) Sample

Human sera of 12 cases were used as samples. And physiological saline solution (0.85% NaCl) and a CRP calibrator set (CRP concentration: 0.01, 0.03, 0.05, 0.2 and 0.3 mg/mL, made by Wako Pure Chemical Industries, Ltd.) were used as samples for preparation of a calibration curve.

(2) Reagents i) Test Solution No. 1

A solution of 100 mM HEPES-NaOH buffer (pH 7.0) containing 0.5% of the predetermined polymer as the agglutination accelerator, 0.1% of BSA and 1% of NaCl was designated as test solution No. 1.

ii) Test Solution No. 2

The anti-human CRP antibody sensitized (immobilized) latex test solution prepared in Example 1 (1) was used as test solution No. 2.

(3) Assay Method

Absorbance measurements for samples were performed under the following measuring conditions by using a BM-8 automatic analyzer made by JEOL Ltd.

A value of absorbance obtained by measuring absorbance of physiological saline solution was used as a reagent blank value.

A calibration curve was prepared from the values obtained by subtracting the reagent blank values from the absorbance values obtained by measuring each standard solution of the CRP calibrator set, and the CRP concentration of each standard solution. Thereafter, the value obtained by subtracting the reagent blank value from the absorbance value obtained by measuring the sample was applied to the calibration curve to obtain a CRP concentration in the human serum.

| Sample: | 1.25 µl |
|---|---|
| Test solution No. 1: | 75 µl |
| Test solution No. 2: | 25 µl |
| Assay method: | 2 point end method (34-65) |
| Main wavelength: | 571 nm |

(4) Results

CRP concentrations (ng/mL) obtained are shown in Table 4.

Comparative Example 3

Assay of CRP Concentration in Human Serum by LT Auto Wako

Measurement by the same method as Referential Example 2 was repeated except that LT Auto Wako (made by Wako Pure Chemical Industries, Ltd.) was used as a reagent. The thus obtained CRP concentrations (ng/mL) are shown in Table 4 together with the results of Referential Example 2.

TABLE 4

| Serum Specimen | Referential Example 2 (ng/mL) | | | Comparative Example 3 (ng/mL) |
|---|---|---|---|---|
| | Polymer 1 | Polymer 5 | Polymer 6 | LT Auto Wako |
| 1 | 0.1 | 0.2 | 0.2 | 0.2 |
| 2 | 0.3 | 0.4 | 0.5 | 0.4 |
| 3 | 0.4 | 0.4 | 0.6 | 0.5 |
| 4 | 1.0 | 1.1 | 1.1 | 1.1 |
| 5 | 1.6 | 1.7 | 1.8 | 1.7 |
| 6 | 1.9 | 2.0 | 2.1 | 2.1 |
| 7 | 3.1 | 3.2 | 3.2 | 3.1 |
| 8 | 9.6 | 9.7 | 9.6 | 9.6 |
| 9 | 10.6 | 10.6 | 10.6 | 10.5 |
| 10 | 12.9 | 13.0 | 12.7 | 12.7 |
| 11 | 17.7 | 17.8 | 17.6 | 17.8 |
| 12 | 18.6 | 18.9 | 18.6 | 18.8 |
| Average | 6.5 | 6.6 | 6.5 | 6.5 |

As obvious from the results in Table 4, the assay results obtained by the method of the present invention are equivalent to the measured values using the LT Auto Wako as the reagent for a conventional assay method, and it can be understood that the assay method of the present invention shows a high correlation to the conventional assay method, in other words, an target substance can be assayed with a high precision without generating non-specific reaction by using the polymer of the present invention.

Referential Example 3

Assay of CRP by Turbidimetric Immunoassay

TIA

Effect of Polymer Type on Agglutination Accelerating Action (1) Sample

Physiological saline solution (0.85% NaCl) was used as a sample for reagent blank assay, and a CRP calibrator set (CRP concentration: 0.01, 0.03, 0.05, 0.2 and 0.3 mg/mL, made by Wako Pure chemical Industries, Ltd.) was used as samples for the CRP-specific absorbance measurement.

(2) Reagents i) Test solution No. 1

A solution of 50 mM HEPPSO-NaOH buffer (pH 8.2) containing 1% of predetermined polymer as an agglutination accelerator and 1% of NaCl, or a solution of 50 M HEPPSO-NaOH buffer (pH 8.2) containing 1% of NaCl as a reagent without agglutination accelerator was designated as test solution No. 1.

ii) Test Solution No. 2

CRPα Auto wako antibody solution (made by Wako Pure Chemical Industries, Ltd.) was used as test solution No. 2.

(3) Assay Method

Assay was performed under the following measuring conditions by using an automatic analyzer 7150 made by Hitachi, Ltd.

| | |
|---|---:|
| Sample: | 10 μl |
| Test solution No. 1: | 250 μl |
| Test solution No. 2: | 50 μl |
| Assay method: | 2 point end method (24-50) |
| Main wavelength: | 340 nm |
| Sub-wavelength: | 700 nm |

(4) Results

The values of absorbance (turbidity) obtained are shown in Table 5. The column indicating CRP concentration of 0.01 to 0.3 (mg/mL) in Table 5 shows the values obtained by subtracting the absorbance values of the reagent blank from the absorbance values obtained for the CRP calibrator set, then multiplying by 10,000. Further, the column indicating reagent blank shows the values obtained by measuring reagent blank under the conditions so that an absorbance of the purified water becomes 0, then multiplying by 10,000.

(CRP concentration: 0.01, 0.03, 0.05, 0.2 and 0.3 mg/mL, made by Wako Pure Chemical Industries, Ltd.) was used as samples for the CRP-specific absorbance measurement.

(2) Reagents i) Test Solution No. 1

A solution of 50 mM HEPPSO-NaOH buffer (pH 8.2) containing the predetermined concentration of polymer 1 as an agglutination accelerator and 1% of NaCl was designated as test solution No. 1.

ii) Test Solution No. 2

CRPα Auto Wako antibody solution (made by Wako Pure Chemical Industries, Ltd.) was used as test solution No. 2.

(3) Assay Method

Assay was performed under the following measuring conditions by using an automatic analyzer 7150 made by Hitachi, Ltd.

| | |
|---|---:|
| Sample: | 10 μl |
| Test solution No. 1: | 250 μl |
| Test solution No. 2: | 50 μl |
| Assay method: | 2 point end method (24-50) |
| Main wavelength: | 340 nm |
| Sub-wavelength: | 700 nm |

(4) Results

The values of absorbance (turbidity) obtained are shown in Table S. The column indicating CRP concentration of 0.01 to 0.03 (mg/mL) in Table 5 shows the values obtained by subtracting the absorbance values of the reagent blank from the absorbance values obtained for the CRP calibrator set, then multiplying by 10,000. Further, the column indicating

TABLE 5

| CRP (mg/ml) | Without agglutination promoter | Referential Example 3 | | | | | | | |
|---|---|---|---|---|---|---|---|---|---|
| | | Polymer 1 | Polymer 2 | Polymer 3 | Polymer 4 | Polymer 5 | Polymer 6 | Polymer 7 | Polymer 8 |
| Reagent Blank | 198 | 177 | 188 | 187 | 173 | 189 | 188 | 201 | 211 |
| 0.01 | 5 | 52 | 10 | 6 | 16 | 21 | 13 | 25 | 59 |
| 0.03 | 26 | 142 | 57 | 32 | 87 | 112 | 93 | 139 | 218 |
| 0.05 | 57 | 264 | 106 | 75 | 150 | 208 | 162 | 264 | 396 |
| 0.20 | 385 | 1476 | 723 | 456 | 976 | 1327 | 1174 | 1478 | 2110 |
| 0.30 | 668 | 2770 | 1261 | 876 | 1829 | 2388 | 2136 | 2545 | 3376 |

According to the results in Table 5, in an assay of CRP by TIA, the agglutination accelerating action was also observed with any polymer of the present invention. Further, in any polymer, the reagent blank values were equal to the cases using reagents without the agglutination accelerators, and non-specific reaction was not observed.

Referential Example 4

Assay of CRP by TIA

Effect of Polymer Concentration on Agglutination Accelerating Action (1) Sample

Physiological saline solution (0.85% NaCl) was used as a sample for reagent blank assay, and a CRP calibrator set reagent blank shows the values obtained by measuring reagent blank under the conditions so that an absorbance of the purified water becomes 0, then multiplying by 10,000.

TABLE 6

| CRP (mg/ml) | Referential Example 4 | | | |
|---|---|---|---|---|
| | 0% | 0.5% | 1% | 2% |
| Reagent Blank | 192 | 189 | 177 | 186 |
| 0.01 | 3 | 10 | 52 | 77 |
| 0.03 | 32 | 61 | 142 | 212 |
| 0.05 | 66 | 122 | 264 | 380 |
| 0.2 | 403 | 842 | 1476 | 1845 |
| 0.3 | 717 | 1597 | 2770 | 3203 |

According to the results in Table 6, it can be understood that the agglutination accelerator action of polymer 1 in the assay by TIA is increased depending on the increase in the concentration of polymer 1. Further, the reagent blank values were almost constant even with increased polymer concentration, and non-specific reaction was not observed.

Referential Example 5

Assay of CRP in Human Serum (1) Sample

Human sera of 26 cases were used as samples.

Physiological saline solution (0.85% NaCl) and a CRP calibrator set (CRP concentration: 0.01, 0.03, 0.05, 0.2 and 0.3 mg/mL, made by Wako Pure Chemical Industries, Ltd.) were used as samples for preparation of a calibration curve.

(2) Reagents i) Test Solution No. 1

A solution of 50 mM HEPPSO-NaOH buffer (pH 8.2) containing 2. St of polymer 5 as an agglutination accelerator and 11 of NaCl was designated as test solution No. 1.

ii) Test Solution No. 2

CRPα Auto Wako antibody solution (made by Wako Pure Chemical Industries, Ltd.) was used as test solution No. 2.

(3) Assay Method

Assay was performed under the following measuring conditions by using an automatic analyzer 7150, made by Hitachi, Ltd. according to the assay method for CRPα Auto Wako.

A value of absorbance obtained by measuring absorbance of physiological saline solution was used as a reagent blank value. A calibration curve was prepared from the CRP concentration of each standard solution and the values obtained by subtracting the reagent blank values from the absorbance values obtained by measuring each standard solution of the CRP calibrator set. Thereafter, the value obtained by subtracting the reagent blank value from the absorbance value obtained by measuring the sample was applied to the calibration curve to obtain a CRP concentration in the human serum.

| | |
|---|---|
| Sample: | 10 µl |
| Test solution No. 1: | 250 µl |
| Test solution No. 2: | 50 µl |
| Assay method: | 2 point end method (24-50) |
| Main wavelength: | 340 nm |
| Sub-wavelength: | 700 nm |

Comparative Example 4

Assay of CRP Concentration in Human Serum by CRPα Auto Wako

Measurements by the same method as Referential Example 5 were repeated except that test solution No. 1 of CRPα Auto Wako (made by Wako Pure chemical Industries, Ltd.) was used as the test solution No. 1 of reagent.

A correlation between the CRP concentrations (mg/mL) obtained and the CRP concentrations (mg/mL) obtained in the above Referential Example S is shown in FIG. 1. In FIG. 1, the correlation equation was: $Y=1.010X-0.04$, and the correlation coefficient was: $r=0.9999$.

As obvious from the above results, it can be understood that the assay results of CRP obtained by the method of the present invention show a high correlation to the assay results of CRP using the conventional assay method, CRPα Auto Wako, in other words, a target substance can be assayed with a high precision without generating non-specific reaction by using the polymer of the present invention.

Referential Example 6

Assay of Rheumatoid Factor (RF) by TIA

Effect of Polymer Type on Agglutination Accelerating Action (1) Sample

Physiological saline solution (0.85% NaCl) was used as a sample for reagent blank assay, and a RF TIA calibrator set (RF concentration: 37, 71, 156, 310 and 498 IU/ml, made by Wako Pure Chemical Industries, Ltd.) was used as samples for the RF-specific absorbance measurements.

(2) Reagents i) Test Solution No. 1

A solution of 50 mM HEPES-NaOH buffer (pH 7.4) containing 1% of the predetermined polymer as an agglutination accelerator and 4% of NaCl, or a solution of 50 mM HEPES-NaOH buffer (pH 7.4) containing 4% of NaCl as a reagent without agglutination accelerator was designated as test solution No. 1.

ii) Test Solution No. 2

A RF-HA Test Wako RF reaction test solution (made by Wako Pure Chemical Industries, Ltd.) was designated as test solution No. 2.

(3) Assay Method

Assay was performed under the following measuring conditions by using an automatic analyzer 7150 made by Hitachi, Ltd.

| | |
|---|---|
| Sample: | 15 µl |
| Test solution No. 1: | 250 µl |
| Test solution No. 2: | 75 µl |
| Assay method: | 2 point end method (24-50) |
| Main wavelength: | 340 nm |
| Sub-wavelength: | 700 nm |

(4) Results

The value of absorbance (turbidity) obtained are shown in Table 7. The columns indicating RF concentration 37 to 498 (IU/mL) in Table 7 shows the values obtained by subtracting the absorbance values of the reagent blank from the absorbance values obtained for the CRP calibrator set, then multiplying by 10,000. Further, the column indicating reagent blank shows the values obtained by measuring reagent blank under the conditions so that an absorbance of the purified water becomes 0, then multiplying by 10,000.

TABLE 7

| RF (IU/ml) | Without Agglutination Promoter | Referential Example 6 | | | | | |
|---|---|---|---|---|---|---|---|
| | | Polymer 1 | Polymer 2 | Polymer 3 | Polymer 4 | Polymer 5 | Polymer 6 |
| Regent Blank | 111 | 128 | 133 | 138 | 132 | 121 | 114 |
| 37 | 3 | 8 | 4 | 4 | 10 | 15 | 2 |
| 71 | 9 | 85 | 15 | 20 | 25 | 71 | 40 |
| 156 | 133 | 464 | 215 | 183 | 316 | 458 | 392 |
| 310 | 794 | 1192 | 938 | 897 | 1043 | 1217 | 1166 |
| 498 | 1525 | 1902 | 1679 | 1643 | 1866 | 1928 | 1941 |

According to the results in Table 7, the agglutination accelerating action was observed in an assay of RF by TIA, by using any polymer of the present invention. Further, in every polymer, the reagent blank values were equal to the cases using reagents without the agglutination accelerator, and non-specific reaction was not observed.

Referential Example 7

Assay of Rheumatoid Factor (RF) by TIA

Polymer Concentration and Agglutination Accelerating Action

The same reagent as Referential Example 6 was used and the same measurements as Referential Example 6 were repeated except that the predetermined concentration of polymer 6 was used as an agglutination accelerator.

(1) Results

The values of absorbance (turbidity) obtained are shown in Table B. The columns indicating RF concentration 37 to 498 (IU/mL) in Table 8 show the values obtained by subtracting the absorbance values of the reagent blank from the absorbance values obtained for the CRP calibrator set, then multiplying by 10,000. Further, the column indicating reagent blank shows the values obtained by measuring reagent blank under the conditions so that an absorbance of the purified water becomes 0, then multiplying by 10,000.

TABLE 8

| RF (IU/ml) | Referential Example 6 | | | | |
|---|---|---|---|---|---|
| | 0% | 0.5% | 1% | 2% | 3% |
| Reagent Blank | 111 | 118 | 114 | 110 | 97 |
| 37 | 3 | 3 | 2 | 32 | 156 |
| 71 | 9 | 15 | 40 | 189 | 377 |
| 156 | 133 | 254 | 392 | 654 | 872 |
| 310 | 794 | 1042 | 1166 | 1466 | 1707 |
| 498 | 1525 | 1997 | 1941 | 2223 | 2495 |

According to the results in Table 8, it can be understood that the agglutination accelerator action of polymer 6 in the assay by TIA is increased depending on the increase in the concentration of polymer 6. Further, the reagent blank values were almost constant even with increased polymer concentration, and non-specific reaction was not observed.

What is claimed is:

1. An immunoassay method of a prostate-specific antigen comprising:
    performing an antigen-antibody reaction comprising, contacting a sample with an antibody to a prostate-specific antigen in the presence of a copolymer as an agglutination accelerator, which is dissolved in a reagent, and is obtained by polymerizing a monomer represented by the following general formula [2]:

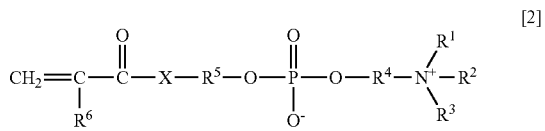

wherein, $R^1$-$R^3$ are each independently a hydrogen atom or an alkyl group optionally having a hydroxyl group; $R^4$ is an alkylene group; $R^5$ is an alkylene group optionally having a substituent and optionally having an oxygen atom in the chain; $R^6$ is a hydrogen atom or a methyl group; and X is an oxygen atom or a —NH— group, and an aralkyl methacrylate;
    measuring a degree of agglutination derived from the antigen-antibody reaction; and
    determining an amount of prostate-specific antigen in the sample based on the degree of agglutination derived from the antigen-antibody reaction.

2. The immunoassay method according to claim 1, wherein the aralkyl methacrylate is benzyl methacrylate.

3. The immunoassay method according to claim 2, wherein a ratio of the monomer unit derived from the monomer represented by the general formula [2] in the copolymer is 20% or more but less than 100%.

4. The immunoassay method according to claim 3, wherein a molecular weight of the polymer is 10,000 to 1,000,000.

5. A kit of reagent for immunoassay of a prostate-specific antigen comprising:
    a reagent containing a copolymer as an agglutination accelerator, which is dissolved in the reagent, and obtained by polymerizing a monomer represented by the following general formula [2]:

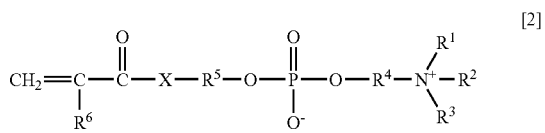

wherein, $R^1$-$R^3$ are each independently a hydrogen atom or an alkyl group optionally having a hydroxyl group; $R^4$ is an alkylone group; $R^5$ is an alkylene group optionally having a substituent and optionally having an oxygen atom in the chain; $R^6$ is a hydrogen atom or a methyl group; and X is an oxygen atom or a —NH— group, and an aralkyl methacrylate; and a reagent containing an antibody to a prostate-specific antigen or a prostate-specific antigen.

6. The kit according to claim 5, wherein the antibody to a prostate-specific antigen or the prostate-specific antigen is supported on a carrier.

7. The kit according to claim 6, wherein the carrier is latex.

8. The kit according to claim 5, wherein the aralkyl methacrylate is benzyl methacrylate.

* * * * *